(12) United States Patent
Mohar et al.

(10) Patent No.: US 8,889,873 B2
(45) Date of Patent: Nov. 18, 2014

(54) PROCESS FOR THE PREPARATION OF ENANTIOMERICALLY ENRICHED PROTON PUMP INHIBITORS

(75) Inventors: Barbara Mohar, Ljubljana (SI); Renata Toplak Casar, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 447 days.

(21) Appl. No.: 13/124,082

(22) PCT Filed: Oct. 13, 2009

(86) PCT No.: PCT/EP2009/063314
§ 371 (c)(1),
(2), (4) Date: Oct. 4, 2011

(87) PCT Pub. No.: WO2010/043601
PCT Pub. Date: Apr. 22, 2010

(65) Prior Publication Data
US 2012/0046319 A1    Feb. 23, 2012

(30) Foreign Application Priority Data
Oct. 14, 2008   (EP) ..................................... 08166571

(51) Int. Cl.
*C07D 401/12*    (2006.01)
(52) U.S. Cl.
CPC .................................... *C07D 401/12* (2013.01)
USPC ....................... 546/273.7; 546/121; 548/307.1
(58) Field of Classification Search
USPC .............................. 546/121, 273.7; 548/307.1
See application file for complete search history.

(56) References Cited

U.S. PATENT DOCUMENTS

| 2005/0096260 A1 | 5/2005 | Ueno et al. |
| 2008/0193531 A1 | 8/2008 | Hermelin et al. |
| 2010/0094037 A1 * | 4/2010 | Katsuki et al. ................. 556/150 |

FOREIGN PATENT DOCUMENTS

| WO | WO 2004/074285 A1 | 9/2004 |
| WO | WO 2005/011691 A1 | 2/2005 |
| WO | WO 2007/140608 A1 | 12/2007 |
| WO | WO 2008/111563 A1 | 9/2008 |

OTHER PUBLICATIONS

Choi et al., "Efficient Asymmetric, etc.," Bull. Korean Chem. Soc. 2008, vol. 29(10), 1879-1880.*
Carreno, "Applications of Sulfoxides, etc.," Chem. Rev. 1995, 95, 1717-1760.*
Bonchio et al., "The First chiral, etc." J. Org. Chem. 1999, 54, 1326-1330.*
Dorwald, Side Reactions in Organic Synthesis, 2005, Wiley: VCH Weinheim Preface, pp. 1-15 & Chapter 8, pp. 279-308.*
H. Cotton, et al.: "Asymmetric Synthesis of Esomeprazole", Tetrahedron Asymmetry, Pergamon, Oxford; GB, vol. 11, No. 18, Sep. 22, 2009, pp. 3819-3825 (XP004224163) (Abstract Only).

* cited by examiner

*Primary Examiner* — Patricia L Morris
(74) *Attorney, Agent, or Firm* — Arent Fox LLP

(57) ABSTRACT

The invention discloses a process for the preparation of compounds having structures typical for proton pump inhibitors in enantiomerically enriched form by using particular metal catalysts in an enantioselective oxidation step. Also disclosed are useful further processes and pure intermediate and subsequently final products.

12 Claims, No Drawings

PROCESS FOR THE PREPARATION OF ENANTIOMERICALLY ENRICHED PROTON PUMP INHIBITORS

CROSS-REFERENCE TO RELATED APPLICATION

This is a 371 National Stage entry of International Application No. PCT/EP2009/063314, filed 13 Oct. 2009, now WO 2010/043601A1 published 22 Apr. 2010, which claims benefit to European Patent Application No. 08166571.3 filed 14 Oct. 2008, the entire contents of which are incorporated herewith in their entirety by reference.

FIELD OF THE INVENTION

The present invention relates to a novel industrially applicable process for the preparation of enantiomerically enriched omeprazole and other related proton pump inhibitors. The process comprises an asymmetric oxidation of the corresponding sulfide by means of an oxygen atom donor catalyzed by a metal complex of an optically active salen or salan type ligand.

BACKGROUND OF THE INVENTION

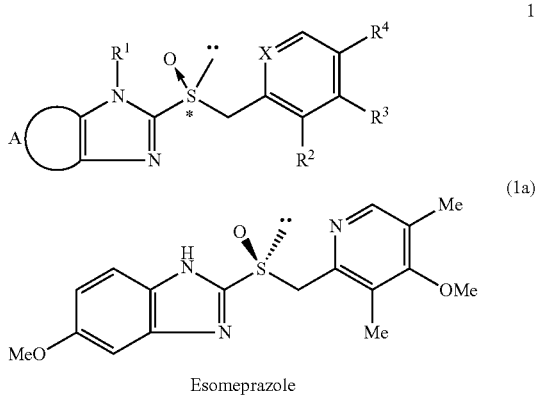

Esomeprazole

Pyridinylmethylsulfinyl benzimidazoles and analogs which belong to a group of compounds of the formula 1 are proton pump inhibitors (PPI) that are widely used for the treatment of gastro-oesophageal reflux disease (GERD) and other acid associated diseases. The first proton pump inhibitor used in the clinical practice is known by its generic name omeprazole. Chemically, it is 5-methoxy-2-[[(4-methoxy-3, 5-dimethyl-2-pyridinyl)methyl]sulfinyl]-1H-benzimidazole and was first disclosed in EP 0005129. The other structurally related proton pump inhibitors are rabeprazole or pariprazole, pantoprazole, lansoprazole, leminoprazole, and tenatoprazole. Pyridinylmethyl-sulfinyl benzimidazoles and analogs belong to a group of chiral sulfoxides. The stereochemical structure of these compounds affects their physicochemical properties. Thus, the S-enantiomer of omeprazole commonly referred as esomeprazole (1a) is said to have improved pharmacokinetical properties which give an improved therapeutic profile such a lower degree of inter-individual variation (WO 94/27988). Esomeprazole magnesium, the generic name for magnesium bis(5-methoxy-2-[(S)-[(4-methoxy-3,5-dimethyl-2-pyridinyl)methyl]sulfinyl]-1H-benzimidazole), is a well-known gastric proton-pump inhibitor and has been commercially available from AstraZeneca under the brand name NEXIUM™ since 2001.

Due to advantageous physiochemical properties of certain enantiomerically pure compounds there is a great need for simple and industrially applicable processes for their preparation. Enantiomerically pure compounds can be obtained either by resolution techniques or asymmetric synthesis. There are processes for resolution of different substituted 2-(2-pyridinylmethylsulphinyl)-1H-benzimidazoles disclosed in the prior art, described in DE 4035455 and WO 94/27988. The disclosed processes involve synthetic steps wherein a diastereomeric mixture is synthesized from the racemate of the corresponding substituted 2-(2-pyridinylm ethylsulphinyl)-1H-benzimidazoles. The following separation of the diastereomers involves complicated separation steps and a large amount of waste is generated.

One of the most efficient methods for enantioselective sulfoxidation is modified Sharpless procedure, developed by Kagan (Pitchen, P.; Deshmukh, M.; Dunach, E.; Kagan, H. B. *J. Am. Chem. Soc.* 1984, 106, 8188). The Kagan protocol is applied for the preparation of enantiomerically enriched pyridinylmethylsulfinyl benzimidazoles, especially esomeprazole, disclosed in the patent WO 96/02535. The oxidation of sulfides is carried out in an organic solvent with an oxidizing agent—a hydroperoxide derivative, preferably cumene hydroperoxide, in the presence of a titanium-diethyl tartrate catalyst and optionally in the presence of a base. The amount of catalyst is near equimolar and the method does not work well with convenient hydrogen peroxide. The patent application US 2003/0171591 describes an improved said process. Another similar method (WO 2004/052882) describes an asymmetric sulfoxidation using chiral zirconium or hafnium complex with tartaric acid esters or amides as catalysts.

The patent application WO 03/089408 discloses an asymmetric oxidation using a catalyst comprising of titanium or vanadium complexed with a chiral S-(+)- or R-(–)-methyl mandelate ligand. The general reaction conditions are similar as in the patent WO 96/02535; oxidation is performed preferably with cumene hydroperoxide in an organic solvent and in the presence of a base. Again, main deficiencies are not solved.

The patent application WO 2004/087702 describes a process for the enantioselective preparation of sulfoxides (from pyridinylmethylsulfinyl benzimidazoles or pyridinylmethylsulfinyl imidazopyridyles) using an oxidizing agent (usually aqueous $H_2O_2$ or $H_2O_2$.urea complex) in the presence of a tungsten or vanadium based catalysts with a chiral amino alcohols. The method is efficient for preparation of enantiomers of tenatoprazole while it is surprisingly less suitable for preparation of esomeprazole.

Further methods to obtain enantiopure pyridinylmethylsulfinyl benzimidazoles, especially esomeprazole, via enantioselective oxidation are described in:

IN 2003MU00503 (Abstract) indicating use of catalyst comprising Ti or V complexed with monodentate ligand;
WO 2008018091 using catalyst comprising chiral Ti isopropoxide and tartrate complex;
CN 1810803 A (Abstract) indicating use of catalyst comprising Ti alkoxide and chiral bidentate ethylene glycol complex;
WO 2007088559 using catalyst comprising V alkoxide and chiral ligand;
CN 101012141 A (Abstract) indicating use of catalyst comprising Ti or Zr alkoxide and chiral β-amino acids; and
CN 1995037 A (Abstract) indicating use of catalyst comprising tartrate and V alkoxide.

A chiral catalyst for the asymmetric oxidation comprising Schiff base ligands known as salen ligands (general formula 2) was first disclosed in the patent application WO 91/14694 by E.N. Jacobsen and coworkers and published in Journal of Organic Chemistry 1991, 56, 2296.

Jacobsen-type catalysts based on mangan-salen complexes (see general formula 2) are now routinely used in asymmetric epoxidations. However, their use in enantioselective oxidation of sulfides to sulphoxides is less explored. First disclosure of asymmetric oxidation of prochiral sulfides was published in patent application WO 93/03838, Tetrahedron Letters 1992, 33, 7111, and Chem. Lett. 1995, 335. First practical application of the said method is the preparation of armodafinil (Tetrahedron: *Asymmetry* 2007, 18, 2959). All published methods are focused on aryl methyl sulfides. None of the methods describes an oxidation of prochiral sulfides in which substituted aromatic or heteroaromatic rings are placed on both sides of sulphur atom as it is in the molecular structure of various proton pump inhibitors.

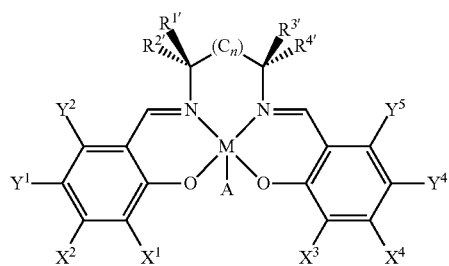

2

Another sulfoxidation of aryl methyl sulfides using vanadium-salan complexes of the formula 3 is also known (Journal of Organic Chemistry 2004, 69, 8500). However, synthesis of manganese complexes of salan ligands and their use in asymmetric oxidation is unknown.

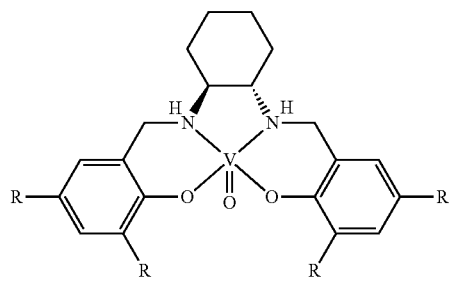

3

There is still a need for an efficient method of preparation of proton pump inhibitors.

SUMMARY OF THE INVENTION

The present invention provides a process for the preparation of a compound of the formula 1 from the corresponding sulfide compound of the formula 4:

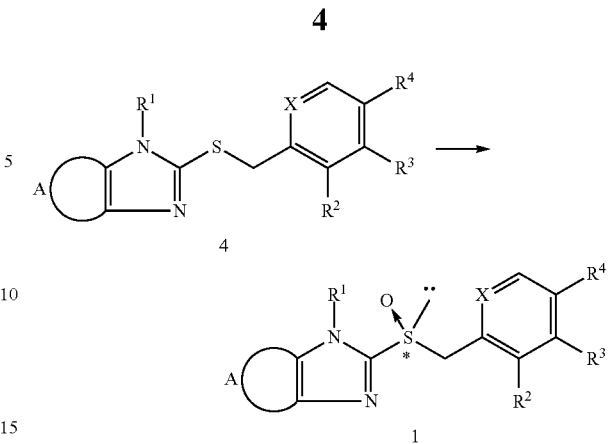

wherein:
S* represents a chiral sulfur atom;
ring A represents benzene or pyridine ring optionally having 1-4 substituents such as halide, cyano, nitro, an alkyl selected from $C_1$-$C_6$ optionally substituted, an aryl, hydroxy, $OR^5$ or $C(O)R^5$ or $COOR^5$ wherein $R^5$ is selected from $C_1$-$C_6$ alkyl or aryl, a 3-10 membered carbocyclic or heterocyclic ring;
X represents a nitrogen atom or C—Y wherein Y is $NH_2$, an N-containing heterocyclic ring or $NR^6R^7$ wherein $R^6$ or $R^7$ are independently selected from a hydrogen atom, $C_1$-$C_6$ alkyl or aryl, a 3-10 membered carbocyclic or heterocyclic ring, or Y is $C(O)R^8$, wherein
$R^8$ is selected from $C_1$-$C_6$ alkyl or aryl, a 3-10 membered carbocyclic or heterocyclic ring;
$R^1$ represents a hydrogen atom, or is selected from $C_1$-$C_6$ alkyl, $C(O)R^9$ or $COOR^9$; $R^9$ selected from $C_1$-$C_6$ alkyl;
$R^2$, $R^3$, $R^4$ can be a hydrogen atom, or selected from $C_1$-$C_6$ alkyl, $OR^{10}$, $COOR^{19}$; selected from $C_1$-$C_6$ alkyl or aryl;
in a solvent through enantioselective oxidation using oxygen atom donor in the presence of a metal complex which is prepared from an optically active ligand, which is selected from the group consisting of:
salen-type complexing ligands,
salan-type complexing ligands, and
complexing ligands having bidentate, tridentate or tetradentate azomethine or hydrogenated azomethine groups;
and a metal precursor.

Salen-type complexing ligands can be preferably defined by the following general formula 5:

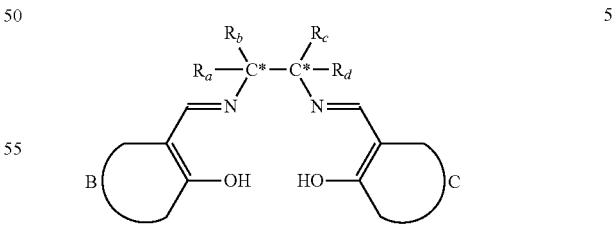

5 wherein:
C* represents an asymmetric carbon atom;
rings B and C represent different or identical, substituted or un-substituted, aromatic or heteroaromatic, monocyclic or polycyclic moiety;
$R_a$, $R_b$, $R_d$ represent substituens which can be selected from the group consisting of hydrogen atom, alkyls such as methyl, ethyl, propyl, iso-propyl, n- or tert-butyl, aryls, optionally wherein substituents may be linked to each other forming a 3-6 atom hydrocarbon chain, wherein the substitutents independently may bear hetero atoms. Alkyl substituents can be linked in such a way they are trans to each other in the aforementioned "compounds".

Salan-type complexing ligands can be preferably defined by the following general formula 6:

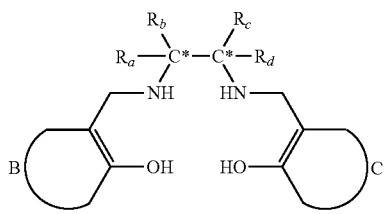

6 wherein:
C* represents an asymmetric carbon atom;
rings B and C represent different or identical, substituted or un-substituted aromatic or heteroaromatic, monocyclic or polycyclic moiety;
$R_a$, $R_b$, $R_c$, $R_d$ represent substituens which can be selected from the group consisting of hydrogen atom, alkyls such as methyl, ethyl, propyl, iso-propyl, n- or tert-butyl, aryls, optionally wherein substituents may be linked to each other forming a 3-6 atom hydrocarbon chain, wherein the substitutents independently may bear hetero atoms. Alkyl substituents can be linked in such a way they are trans to each other in the aforementioned "compounds".

Complexing ligands analogous to salen-type or salan-type complexing ligands (sometimes referred herein as "analogous complexing ligands"), each having bidentate, tridentate or tetradentate azomethine or hydrogenated (reduced form of) azomethine groups can be preferably defined by the following general formulae 7 and 8:

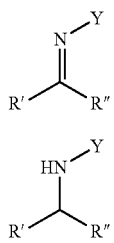

7

8 wherein:
Y is $CR^{III}R^{IV}$ substituent in case of azomethine or hydrogenated azomethine complexing ligands or macrocyclic ligands such as corrin compounds and porphyrine compounds, or
Y is OH substituent in case of dioxime, glyoxime, salicylaldoxime ligands;
$R^I$, $R^{II}$, $R^{III}$, $R^{IV}$ represent various substituents bearing at least one chiral center. They can be selected from the group consisting of hydrogen atom, alkyls such as methyl, ethyl, propyl, iso-propyl, n- or tert-butyl, aryls, optionally wherein substituents may be linked to each other forming a 3-6 atom hydrocarbon chain, wherein the substituents independently may bear hetero atoms.

Alkyl substituents can be linked in such a way they are trans to each other in the aforementioned "compounds".

Examples for such "analogous complexing ligands" include, without being limited to dioxime compounds, glyoxime compounds and salicylaldoxime compounds, in particular those derived from 1,2-diamines; macrocyclic ligands such as corrin compounds and porphyrine compounds, and the like. For this type of complexing ligands the term "compounds" means substitiuted or unsubstituted compounds which contain at least one chiral center. Substitutions can be selected from the group consisting of hydrogen atom, alkyls such as methyl, ethyl, propyl, iso-propyl, n- or tert-butyl, aryls, wherein substituents may be linked to each other forming a 3-6 atom hydrocarbon chain, wherein the substiutents independently may bear hetero atoms. Alkyl substituents can be linked in such a way they are trans to each other in the aforementioned "compounds".

The metal used for the metal precursor for forming the metal complex is preferably a transition metal. Transition metal elements means the transition elements shown in the Periodic Table of Elements, and concretely, are Sc through Cu in Period 4, Y through Ag in Period 5, La through Au in Period 6, and the like. Transition metal elements may especially be selected from those which are typically known to catalyse oxidation reactions. Transition metal elements are more preferably selected from the group consisting of Mn, Cu, Co, V, Ti, Fe, Cr, and Ru. The metal is most preferably Mn.

Further preferred metal complexes used are prepared in an appropriate solvent and are based on a transition metal and a chiral ligand, contemplating especially those of the general formula 9

$$ML_qX_rL'_v(Sv)_s \qquad 9$$

wherein:
M represents a transition metal selected from the group consisting of Mn, Cu, Co, V, Ti, Fe, Cr, and Ru, wherein M preferably is Mn;
L represents an optically active compound of general formula 10

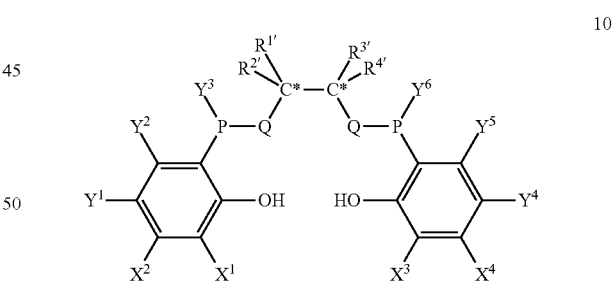

10 wherein:
C* represents an asymmetric carbon atom;
$R^{1'}$ and $R^{4'}$ are identical and selected from either a first group consisting of a hydrogen atom, $CH_3$, $C_2H_5$ or other primary alkyls or from a second group consisting of aryls, secondary or tertiary alkyls and alkyls bearing hetero atoms, or $R^{1'}$ and $R^{4'}$ are linked to each other forming a $C_3$-$C_6$ hydrocarbon chain in such a way that $R^{1'}$ and $R^{4'}$ are trans to each other;
$R^{2'}$ and $R^{3'}$ are identical and are either selected from the said second group if $R^{1'}$ and $R^{4'}$ are selected from the said first group or selected from the said first group if $R^{1'}$ and $R^{4'}$ are selected from the said second group;

X[1] and X[3] are independently selected from the group consisting of aryls, primary, secondary or tertiary alkyls and hetero atoms;

X[2], X[4], Y[1], Y[2], Y[3], Y[4], Y[5] and Y[6] are independently selected from a group consisting of hydrogen atom, halide, alkyl, aryl, or alkyl groups optionally bearing hetero atoms segment P-Q represents C=N or CH—NH
  in which one or more hydrogen atoms on coordinating atoms are optionally removed by coordination to the central metal atom M;

X is an anion which is optionally present to balance metal oxidation state and is selected from the group of inorganic ions such as halogenides (e.g. chloride), $PF_6^-$, $BF_4^-$, $SbF_6^-$, or alkanoates such as acetate, haloalkanoates such as trifluoroacetate, or haloalkanesulfonates such as triflate, and preferably chloride;

L' represents a co-ligand selected from compounds such as N-containing heterocycles (e.g. imidazole, N-methylimidazole), electron donating compounds (e.g pyridin N-oxide derivatives), amines and their salts, chiral amines (e.g. chinconine, chinconidine), ammonium salts (e.g. ammonium carboxylates, benzoates, hydrogencarbonates), and preferably ammonium acetate;

Sv represents a ligand molecule such as $H_2O$, MeOH, EtOH, amine, 1,2-diamine, a ketone such as acetone;

q is an integer varying from 1 to 2, r, v, and s are integers varying from 0 to 2.

Chiral ligand L is especially selected from formulae 10a or 10b as defined below, i.e. salen-type ligand of the formula 10a

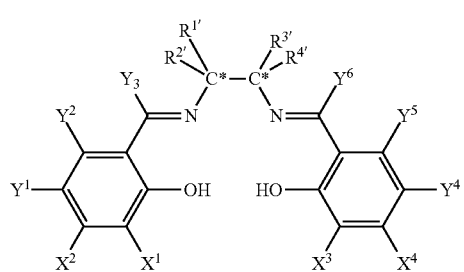

wherein:
C* represents an asymmetric carbon atom;

R[1'] and R[4'] are identical and selected from either groups consisting of a hydrogen atom, $CH_3$, $C_2H_5$ or other primary alkyls or from the second group consisting of aryls, secondary or tertiary alkyls and alkyls bearing hetero atoms, or R[1'] and R[4'] are linked to each other forming a $C_3$-$C_6$ hydrocarbon chain in such a way that R[1'] and R[4'] are trans to each other;

R[2'] and R[3'] are identical and are either selected from the said second group if R[1'] and R[4'] are selected from the said first group or selected from the said first group if R[1'] and R[4'] are selected from the said second group;

X[1] and X[3] are independently selected from the group consisting of aryls, primary, secondary or tertiary alkyls and hetero atoms;

X[2], X[4], Y[1], Y[2], Y[3], Y[4], Y[5] and Y[6] are independently selected from a group consisting of a hydrogen atom, a halide, alkyl, aryl, or alkyl groups optionally bearing hetero atoms;

Or salan-type ligands of the formula 10b:

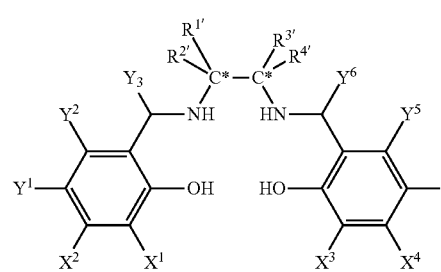

wherein:
C* represents an asymmetric carbon atom;

R[1'] and R[4'] are identical and selected from either groups consisting of a hydrogen atom, $CH_3$, $C_2H_5$ or other primary alkyls or from the second group consisting of aryls, secondary or tertiary alkyls and alkyls bearing hetero atoms, or R[1'] and R[4'] are linked to each other forming a $C_3$-$C_6$ hydrocarbon chain in such a way that R[1'] and R[4'] are trans to each other;

R[2'] and R[3'] are identical and are either selected from the said second group if R[1'] and R[4'] are selected from the said first group or selected from the said first group if R[1'] and R[4'] are selected from the said second group;

X[1] and X[3] are independently selected from the group consisting of aryls, primary, secondary or tertiary alkyls and hetero atoms;

X[2], X[4], Y[1], Y[2], Y[3], Y[4], Y[5] and Y[6] are independently selected from a group consisting of a hydrogen atom, a halide, alkyl, aryl, or alkyl groups optionally bearing hetero atoms.

According to general knowledge that in metal complexes catalyzed reactions changing of the absolute configuration of the ligand leads to formation of the opposite enantiomer of the product, the absolute configuration of the ligand can be chosen according to the desired enantiomer (R or S) to be formed.

The present invention further provides a process for the preparation of a proton pump inhibitor, comprising carrying out a process defined above to obtain a compound of the formula 1; and providing the obtained product of the formula 1 in a pharmaceutically acceptable form. Such providing may preferably be represented by a conversion into a salt form, a step basically known as such. A pharmaceutically acceptable salt may be selected from alkali metals such as sodium or potassium, alkaline earth metals such as calcium, magnesium or strontium, or ammonium salts.

The present invention further provides a compound of formula 1 obtained by enantioselective oxidation using metal catalyst, essentially free of metal catalyst-derived metal:

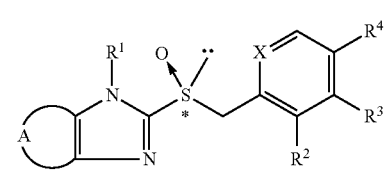

wherein S*, ring A, X and R[1] to R[4] are as defined in claim 1.

As used herein the term "essentially free" can mean entirely free of metal catalyst-derived metal that has been avoided according to the synthesis of the compound, e.g.

entirely free of any one of Ti (IV), V, Zr (IV) and Hf (IV) metals, and even below detection limit, because these metals were not used. The term "below detection limit" used herein typically means below atomic absorption spectroscopy (AAS)—measurable levels, that is for example below of about 10 ppm. Alternatively for the case of the metal that was actually used for the metal-catalyzed oxidation, the term "essentially free" can mean only trace amounts, or up to amounts of daily pharmaceutical dosage forms which are within the limits acceptable according EMEA's Guideline on the specification limits for residue of metal catalysts or metal reagents or limits acceptable according to USP General Chapter on Inorganic Impurities: Heavy Metals. Such maximum limit according to authority regulations is the permitted daily exposure (PDE) for oral non-dietary intake. Accordingly, with respect to examples of metal catalyst-derived metals that may have been actually been used in the synthesis of the compound, the desirably selected numerical upper limit is maximally 2.5 mg/day of Mn (EMEA's Guideline), maximally 2500 µg/day of Cu (EMEA's Guideline), maximally 1000 µg/day of Co (USP), maximally 300 µg/clay of V (EMEA's Guideline), maximally 13 mg/day of Fe (EMEA's Guideline), maximally 250 µg/day of Cr (EMEA's Guideline), and maximally 100 µg/day of Ru (USP), respectively.

Accordingly, suitable dosage forms for compound of formula 1 can be contemplated which satisfy the maximum PDE levels as defined with respect to the respective metal. The dosage form may include descriptions on pharmaceutical packages or package inserts, respectively with an indication about a corresponding number of usable single dosage forms while still keeping within the above-mentioned PDE levels per metal.

According to a particularly preferred embodiment, the term "essentially free" can mean that only Mn is present as being derived from the enantioselective oxidation, whereas other metals may still derive from other procedural steps such as conversion into a desired salt of compound 1, or inclusion of desired excipients in the final pharmaceutical composition. Therefore, according to a particular embodiment in the event that Mn was used in the enantioselective oxidation step, the present invention provides pharmaceutical dosage form(s) in which Manganese (Mn) is present by being detectable, but can be limited to a tolerable range, such as a daily dose defined by the accepted PDE level, i.e. of maximally 2.5 mg/day, preferably maximally 0.5 mg/day, particularly maximally 0.1 mg/day, wherein the pharmaceutical dosage form(s) comprise the compound of formula 1, and one or more pharmaceutically acceptable excipient. The pharmaceutical dosage form can be formed by a single unit or by multiple units for a medical use, while observing the indicated Mn PDE level.

The present invention further provides a process for the preparation of a pharmaceutical composition comprising a proton pump inhibitor according to formula 1 as the active ingredient, comprising the steps of:
a) providing an enantiomerically enriched proton pump inhibitor through enantioselective oxidation using metal catalyst, the provided proton pump inhibitor being essentially free of metal catalyst-derived metal,
b) optionally converting the obtained product of step a) into a pharmaceutically acceptable salt and
c) admixing the thus provided proton pump inhibitor with at least one pharmaceutically acceptable excipient.

Moreover, the present invention provides for a process for the preparation of a pharmaceutical composition comprising a proton pump inhibitor as defined by formula 1 as the active ingredient, comprising the steps of:

a) carrying out a process for the preparation of the compound of formula 1 as disclosed herein,
b) optionally converting the obtained product of the prepared proton pump inhibitor of formula 1 into a pharmaceutically acceptable salt, and
c) admixing the thus provided proton pump inhibitor of formula 1 with at least one pharmaceutically acceptable excipient.

The proton pump inhibitor provided by step a) and/or step b) can be attributed to the synthesis route of metal catalyst-using enantioselective oxidation. This can be determined, for example based on the impurity profile, carry over of starting materials, reagents (e.g. ligand), residual solvents, and especially residual catalyst. Thus the intermediate product of step a) and/or b) is defined by either being "entirely free" (when an undesirable metal has not been used) or "essentially free" (when a desirable metal has been used) as defined above, respectively. In particular with respect to a metal has been used, such as Mn, only well tolerable traces may be present. The maximum PDE levels mentioned above for the respective metals may thus be ensured for the final pharmaceutical composition with respect to the daily dosage thereof. Of course, the final pharmaceutical formulation may contain pharmaceutically acceptable metals, or metals derived from sources other than the metal catalyst.

The pharmaceutical composition and dosage form(s) of the invention are suitable for oral and parenteral administration. The most suitable route of administration as well magnitude of a therapeutic or preventive dose of omeprazole sodium according to the invention in any given case will depend on the nature and severity of the disease to be treated or prevented. The dose and dose frequency may also vary according to the age, body weight, and response of the individual patient. In general, a suitable dose of the active ingredient is within the range of 10 mg to 80 mg daily, preferably between 20 to 40 mg of total daily dosage. Dosage forms include capsules, tablets, dispersions, solutions, suspensions, emulsions, gels, powders. A special dosage form is represented by a dry powder prepared for injections and infusions. Suitable pharmaceutically acceptable excipients are known to the person skilled in the art and correspondingly can be used in the pharmaceutical composition and dosage form(s) of the invention.

The present invention generally makes available a use of a metal complex which is prepared from (i) an optically active ligand, which is selected from the group consisting of salen-type complexing ligands, salan-type complexing ligands, and complexing ligands having bidentate, tridentate or tetradentate azomethine or hydrogenated azomethine groups; and (ii) a metal precursor for the manufacture of a proton pump inhibitor. The metal precursor may contain any transition metal mentioned above.

Moreover, the present invention generally makes available use of a chiral, Mn-containing catalyst compound in a step of enantioselective oxidation to obtain a proton pump inhibitor of the formula 1 defined above. The catalyst compound in the enantioselective oxidation step can contain Mn as metal only; if desired it can be free of other hitherto used transition metals for enantioselective oxidation to obtain a proton pump inhibitor, e.g. free of Ti, V, Hf and Zr.

The present invention further provides a pharmaceutical composition comprising a proton pump inhibitor as an active ingredient and at least one pharmaceutically acceptable excipient, obtainable by the process defined above.

According to preferred embodiments of the present invention, the proton pump inhibitor is selected from the group consisting of omeprazole, rabeprazole, pariprazole, pantoprazole, lansoprazole, leminoprazole and tenatoprazole and their pharmaceutically acceptable salts, preferably in their enantiomerically enriched form. Most preferred proton pump inhibitor is enantiomerically enriched omeprazole.

The pharmaceutical compositions and pharmaceutical dosage forms disclosed herein can be used as a medicament for prevention and/or treatment of a gastrointestinal inflammatory disease or condition.

DESCRIPTION OF ADVANTAGES AND PREFERRED EMBODIMENTS OF THE INVENTION

The present invention is described in the following in further detail by referring to advantages and preferred embodiments, which however are provided for illustrative purpose and shall not be meant to limit the invention in any way.

The invention is concerned with a process for the preparation of compounds having structures typical for proton pump inhibitors in enantiomerically enriched form by using particular chiral metal catalysts in an enatioselective oxidation step. The chiral metal catalysts are diligently selected despite of some structural peculiarities typical for proton pump inhibitors, and surprisingly provide for remarkably limiting the amount of metal catalyst, which significantly effects economical benefits as well as the purity of the intermediate and the final API product of proton pump inhibitor. A further advantage resides in that the metal of the metal catalyst can be more freely chosen. This allows to use non-toxic metals or low-toxic metals for the enatioselective oxidation step. Preferred selection in terms of balance between oxidation efficiency and low toxicity is from the group consisting of Mn, Cu, Co, V, Ti, Fe, Cr, and Ru. Surprisingly, selection of Mn, which is well tolerable for pharmaceutical applications, as the metal for the metal catalyst provides excellent results.

In particular, the present invention discloses a novel industrially applicable process for the preparation of enantiomerically enriched omeprazole and other related proton pump inhibitors of the formula 1 from the corresponding sulfides of the formula 4

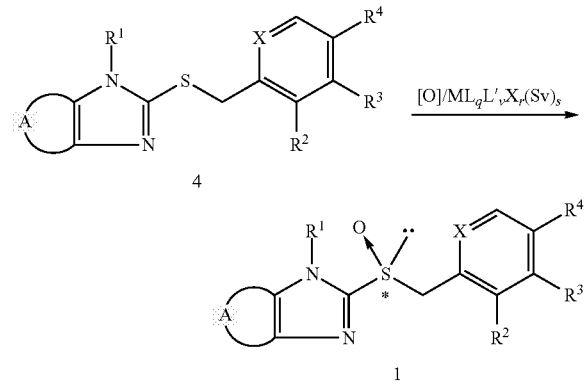

wherein
S* represents a chiral sulfur atom;
ring A represents benzene or pyridine ring optionally having 1-4 substituents such as halide, cyano, nitro, an alkyl selected from $C_1$-$C_6$ optionally substituted, an aryl, hydroxy, $OR^5$ or $C(O)R^5$ or $COOR^5$ wherein $R^5$ is selected from $C_1$-$C_6$ alkyl or aryl, a 3-10 membered carbocyclic or heterocyclic ring;

X represents a nitrogen atom or C—Y wherein Y is $NH_2$, an N-containing heterocyclic ring or $NR^6R^7$ wherein $R^6$ or $R^7$ are independently selected from a hydrogen atom, $C_1$-$C_6$ alkyl or aryl, a 3-10 membered carbocyclic or heterocyclic ring, or Y is $C(O)R^8$, wherein $R^8$ is selected from $C_1$-$C_6$ alkyl or aryl, a 3-10 membered carbocyclic or heterocyclic ring;

$R^1$ represents a hydrogen atom, or is selected from $C_1$-$C_6$ alkyl, $C(O)R^9$ or $COOR^9$; $R^9$ selected from $C_1$-$C_6$ alkyl;

$R^2$, $R^3$, $R^4$ can be a hydrogen atom, or selected from $C_1$-$C_6$ alkyl, $OR^{10}$, $COOR^{10}$; $R^{10}$ selected from $C_1$-$C_6$ alkyl or aryl;
in a solvent through enantioselective oxidation using oxygen atom donor in the presence of a particular metal complex which is prepared from an optically active ligand and a metal precursor as disclosed herein. As desired the obtained product of the formula 1 can be optionally converted into a pharmaceutically acceptable salt.

The present invention thereby allows an advantageous and effective one-step asymmetric oxidation for the preparation of enantiomerically enriched proton pump inhibitors.

Preferably compounds of the formula 4 are selected from sulfide precursors of proton pump inhibitors of omeprazole, rabeprazole, pariprazole, pantoprazole, lansoprazole, leminoprazole and tenatoprazole, most preferably from the sulfide precursor of omeprazole.

The oxidation process is performed in an organic solvent or water or mixture thereof in a temperature range from –40° C. to 40° C. and reaction time between 1 hour and 48 hours.

The metal complexes used in the said enantioselective oxidation are prepared in an appropriate solvent and are based on a metal, in particular a transition metal, and a chiral ligand. Especially metal complexes of the general formula 9 are effective, $$ML_qX_rL'_v(Sv)_s \qquad 9$$

wherein:
M represents a transition metal chosen among Mn, Cu, Co, V, Ti, Fe, Cr, Ru and preferably Mn
L represents an optically active compound of general formula 10a or 10b as defined below in which some hydrogen atoms on coordinating atoms are optionally removed by coordination to the central metal atom;
X is an anion which is optionally present to balance metal oxidation state and is selected from the group of inorganic ions such as halogenides (e.g. chloride), $PF_6^-$, $BF_4^-$, $SbF_6^-$, or alkanoates such as acetate, haloalkanoates such as trifluoroacetate, or haloalkanesulfonates such as triflate, and preferably chloride;
L' represents a co-ligand selected from compounds such as N-containing heterocycles (e.g. imidazole, N-methylimidazole), electron donating compounds (e.g. pyridin N-oxide derivatives), amines and their salts, chiral amines (e.g. chinconine, chinconidine), ammonium salts (e.g. ammonium carboxylates, benzoates, hydrogencarbonates), and preferably ammonium acetate;
Sv represents a ligand molecule such as $H_2O$, MeOH, EtOH, amine, 1,2-diamine, a ketone such as acetone;
q is an integer varying from 1 to 2, r, v, and s are integers varying from 0 to 2.

Metal complexes can be used as preformed complexes or prepared in situ.

Since in metal complex catalyzed reactions, the absolute configuration of the chiral ligand normally leads to formation of the opposite enantiomer of the product, the absolute configuration of the ligand can be correspondingly chosen depending on the desired enantiomer to be formed.

In one preferred embodiment of the invention chiral ligand L is selected from salen-type ligands of the formula 10a

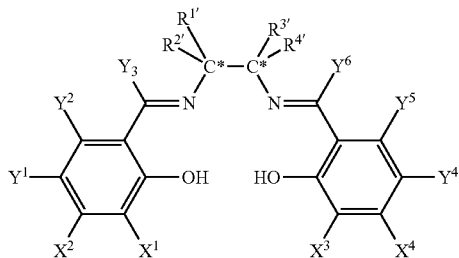

wherein:
C* represents an asymmetric carbon atom;
R$^{1'}$ and R$^{4'}$ are identical and selected from either groups consisting of a hydrogen atom, CH$_3$, C$_2$H$_5$ or other primary alkyls or from the second group consisting of aryls, secondary or tertiary alkyls and alkyls bearing hetero atoms, or R$^{1'}$ and R$^{4'}$ are linked to each other forming a C$_3$-C$_6$ hydrocarbon chain in such a way that R$^{1'}$ and R$^{4'}$ are trans to each other;
R$^{2'}$ and R$^{3'}$ are identical and are either selected from the said second group if R$^{1'}$ and R$^{4'}$ are selected from the said first group or selected from the said first group if R$^{1'}$ and R$^{4'}$ are selected from the said second group;
X$^1$ and X$^3$ are independently selected from the group consisting of aryls, primary, secondary or tertiary alkyls and hetero atoms;
X$^2$, X$^4$, Y$^1$, Y$^2$, Y$^3$, Y$^4$, Y$^5$ and Y$^6$ are independently selected from a group consisting of a hydrogen atom, a halide, alkyl, aryl, or alkyl groups optionally bearing hetero atoms.

A particularly preferred salen-type metal catalyst used is one with a specific structure of the formula 2a shown below:

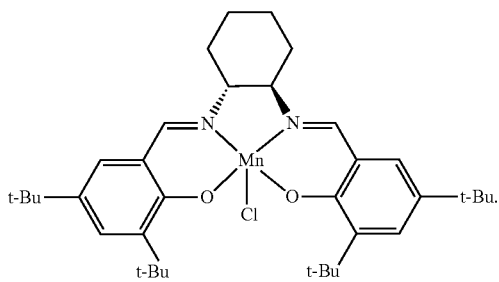

Said catalyst 2a is commercially available and is preferably used as preformed complex.

In another preferred embodiment of the invention chiral ligand L is selected from salan-type ligands of the formula 10b:

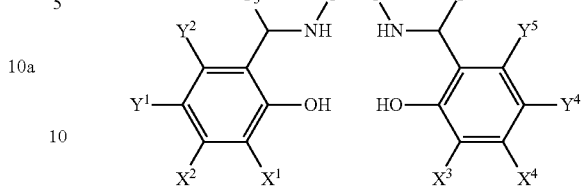

wherein:
C* represents an asymmetric carbon atom;
R$^{1'}$ and R$^{4'}$ are identical and selected from either groups consisting of a hydrogen atom, CH$_3$, C$_2$H$_5$ or other primary alkyls or from the second group consisting of aryls, secondary or tertiary alkyls and alkyls bearing hetero atoms, or and R$^{4'}$ are linked to each other forming a C$_3$-C$_6$ hydrocarbon chain in such a way that R$^{1'}$ and R$^{4'}$ are trans to each other;
R$^{2'}$ and R$^{3'}$ are identical and are either selected from the said second group if R$^{1'}$ and R$^{4'}$ are selected from the said first group or selected from the said first group if R$^{1'}$ and R$^{4'}$ are selected from the said second group;
X$^1$ and X$^3$ are independently selected from the group consisting of aryls, primary, secondary or tertiary alkyls and hetero atoms;
X$^2$, Y$^4$, Y$^1$, Y$^2$, Y$^3$, Y$^4$, Y$^5$ and Y$^6$ are independently selected from a group consisting of a hydrogen atom, a halide, alkyl, aryl, or alkyl groups optionally bearing hetero atoms.

Salan ligands of the formula 10b are not commercially available but they are prepared from the corresponding salenes of the formulas 10a by reduction. A particularly preferred salan-type ligand is a compound of the formula 10c:

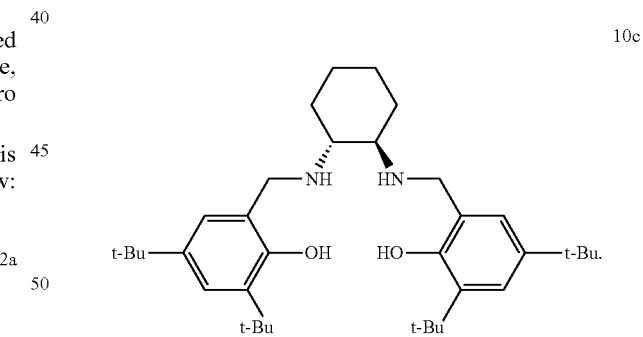

Said metal complexes derived from salen-type ligands of the formula 10a or salan-type ligands of the formula 10b can be prepared by treatment of a solution of an appropriate chiral ligand of the formula 10a or 10b with an appropriate metal salt such as metal acetates, metal halides, metal triflates or acetylacetonates. Preferably acetylacetonates salts are used, for example Mn(III) acetylacetonate, V(IV)O acetylacetonate, Cu (II) acetylacetonate or Fe(III) acetylacetonate. Alternatively, for the preparation of manganese complexes Mn(II) acetate tetrahydrate is preferably used. The reaction is suitably carried out in a polar organic solvent, preferably an alcohol (e.g. methanol, ethanol), at ambient or higher temperature. Optionally, an alkaline metal salt, such as LiCl, LiBr, NaCl is added into the reaction mixture. The mixture is then stirred from 1 to 24 hours, preferably between 2 and 10 hours and in the reaction mixture the said metal complex is formed.

The formed metal complex can be used for further enantioselective oxidations as in situ formed complex, in the same or different solvent, or as an isolated solid—preformed complex.

The metal complex can be precipitated by addition of water and isolated by filtration. Alternatively, the formed metal complex can be isolated by extraction with an organic solvent and precipitated by adding an alkane. Said organic solvent is selected from a group of aromatic organic solvent (e.g. toluene, benzene, chlorobenze, xylene), haloalkanes (e.g. dichloromethane, chloroform) or acetates (e.g. methyl acetate, ethyl acetate, iso-propyl acetate), preferably toluene or dichloromethane are used, and more preferably toluene is used. Said alkane is selected from the group of pentane, hexane, heptane or cycloalkanes such as cyclohexane, preferably used is heptane or hexane.

In the reaction of the invention, enantioselective oxidation of sulfide precursors of proton pump inhibitors of the formula 4 suitable oxidizing agents including, but not limited to hydrogen peroxide, hydrogen peroxide/urea complex, organic peroxides, such as cumene hydroperoxide and tert-butyl hydroperoxide, peroxy acides such as m-chloroperoxybenzoic acid or sodium hypochlorite; preferably hydrogen peroxide solution or hydrogen peroxide/urea complex are used. In the most preferred manner, oxidation is carried out with 30% hydrogen peroxide solution. Oxidizing agent is preferably added to the reaction mixture in an excess amount, for example in the amount of at least 10 mol equivalents, relative to the compound of formula 4. In order to achieve a better enantiomeric excess, slow addition of the oxidizing agent over several hours (3-8 h) is advantageous.

For the completion of asymmetric oxidation for the preparation of pyridinylmethylsulfinyl benzimidazoles of the formula 1 surprisingly low amounts of the metal catalyst as disclosed herein, are used to give satisfactorily results. The use of the specific metal catalyst disclosed herein enables to adjust a range of catalyst between 0.01-0.1 mol equivalent, most preferably between 0.02-0.05 equivalent per mol equivalent of compound of the formula 4. The use of low catalyst amount made possible by the specific metal catalysts is particularly valuable and beneficial. It ensures safety of the drug, as the amount of non-physiological metal cations in a pharmaceutical active ingredient can be effectively controlled and limited.

Limiting the molar ratio of metal catalyst to the compound of the formula 4 is made feasible in particular in cases of using catalyst of the formula 9. In the most preferred examples, the amount of a manganese chiral catalyst of the formula 2a or the analogous complex with the ligand 10c is in a range between 0.01-0.1 mol equivalent, most preferably between 0.02-0.05 equivalent per compound of the formula 4. The amount of the metal catalyst, such as the salen manganese catalyst $(ML_qX_rL'_v(Sv)_s)$, M is Mn, X is halogen, L is 10a, q, r is 1, y, s is 0 or optional) or salan manganese catalyst $(ML_qX_rL'_v(Sv)_s)$, M is Mn, X is halogen, L is 10b, q, r is 1, y, s is 0 or optional) exemplified in the Examples below, does not significantly affect enantioselectivity of the sulfoxidation.

The enatioselective oxidation process may be proceeded in an organic solvent at temperature from −40° C. to 40° C. At first, a solution of a starting pyridylmethylthio-benzimidazole compound of the formula 4 and metal catalyst in an appropriate solvent can be prepared. Suitable solvent for the reaction is an organic solvent, water or a mixture thereof. Said organic solvent is selected from nitriles (e.g. acetonitrile, propionitrile), alcohols (e.g. ethanol, methanol), ketones (e.g. acetone), chlorinated solvents (e.g. dichloromethane, chloroform) and aromatic solvents (e.g. toluene, xylene). The preferred solvent mixtures are acetonitrile-dichloromethane and acetonitrile-water. Then the reaction mixture is cooled to −20 to −5° C., preferably to −10° C. Afterwards, the oxidizing agent can be added, preferably dropwise over a prolonged addition period and in molar excess relative to the starting compound 4. A suitable prolonged addition period is between 1 and 48 hours, preferably between 2 and 15 hours, most preferably about 3 hours. A suitable molar excess which is preferably used is an amount of at least 10 mol equivalents. After the addition of the oxidizing agent is completed, the reaction mixture can be further stirred, for example for additional 4 to 10 hours, suitably 8 hours. Enantiomerically enriched proton pump inhibitors of the formula 1 are formed in the reaction mixture. They may be further isolated with typical isolation and purification procedures known in the art; such methods are extraction, concentration, crystallization, chromatography or a combination thereof.

Preferably, the product is isolated in the following manner. The reaction is quenched by the addition of the reducing reagent selected from a group of aqueous sodium thiosulfate, sodium dithionite, or sodium sulfite. Preferably sodium sulfite is used. In a preferred manner, cold reaction mixture is added into the cold solution of reducing agent at a temperature not exceeding 15° C. Then, the reaction mixture can be extracted twice with organic solvent. Suitable organic solvents for said extraction are organic esters, such as acetates, preferably ethyl acetate or chlorinated organic solvents, preferably dichloromethane. The water phase is discarded and the organic phase is dried over anhydrous $Na_2SO_4$. Then the solvent is evaporated and the oily residue is triturated with aqueous NaOH and extracted with a mixture of toluene/acetonitrile 9:1. The organic phase is discarded and pH in the water phase is adjusted to 9.4 with 1 M HCl. The obtained mixture is extracted with an organic solvent, such as aliphatic ester, the most preferred is ethyl acetate. The water phase is discarded and the organic phase is dried over anhydrous $Na_2SO_4$, filtered and concentrated. The oily residue is dissolved in isooctane followed by evaporation of the solvent. The product obtained is in form of a crispy foam.

Surprisingly, said oxidation process using catalysts of salen-type, salan-type or analogous metal complexes having bidentate, tridentate or tetradentate azomethine or hydrogenated azomethine groups as ligands, preferably using an optically active salen 10a or saian 10b type ligand followed by the described isolation leads to sulfoxide products in a satisfactory chemical yield and enantiomeric excess, although starting prochiral sulfides 4 contain heteroaryl substituents of comparable size, and the substituents may coordinate with the metal. These characteristics of the starting sulfides would have been expected to be particularly undesirable for enantioselective reaction catalyzed by metal catalysts, and would have been expected to distinctively perturb the function of the catalyst resulting in a lower asymmetric induction. Contrary to such prior expectations, and even more surprisingly, much lower amounts of the chiral catalyst could be used to give satisfactorily results, when compared to the previously disclosed diethyl tartrate-titanium, zirconium and hafnium catalyzed oxidation processes. Further, the amount of the added catalyst does not have an influence on enantiomeric excess of the resulting enantiomerically enriched form of pyridinylmethylsulfinyl benzimidazoles 1, and the obtained results are reproducible. A small amount of metal made actually feasible can be effectively removed to reach remarkable pharmaceutical quality. In order to further enhance chemical yield and enantiomeric excess of the asymmetric oxidation process, fine tuning of catalyst structure was performed. The preformed complexes of salan ligands 10b proved to form even better catalysts than complexes of salen ligands 10a in the said enantioselective sulfoxidation process. In the preferred embodiment hydrogen peroxide is used as an oxidizing agent, which makes the present invention advantageous from the environmental point of view. The advantageous effects are made feasible especially when using the manganese catalysts disclosed.

Hence, it has been surprisingly found that the use of salen-type, salan-type or analogous type metal complexes as catalyst, which is prepared as disclosed above, in the oxidation of prochiral sulfides in which substituted aromatic or heteroaromatic rings are placed on both sides of sulphur atom and in which potentially affecting structural groups may be present—as is relevant in the molecular structure of various proton pump inhibitors—, unexpectedly encounters problems of enabling the use of cheap hydrogen peroxide as well as the use of metal catalysts in amounts essentially below equimolar ratios, yet with no discernible or substantial detrimental effect on enantiomeric purity (as determined by enantiomeric excess, ee).

These overall beneficial effects made feasible by the process according to the present invention not only significantly contribute to a more cheap, more environmental-friendly approach to provide enantiomerically enriched proton pump inhibitors. Moreover, they are significant for the constitution of the product, i.e. the compound of formula 1, which in turn has significant consequences for the subsequent processing and thus the final product of active pharmaceutical ingredient when converted to the respective salt form to be included in a pharmaceutical preparation. Without being bound to any theory, it can be believed that the manner, the extend and the timing of limiting metals derived from the catalyst used in the enantiomeric enrichment reaction according to the present invention is important to achieve an extremely high purity, especially with respect to undesirable metal impurities. Firstly, metals previously considered to be required for the catalyst of the enantiomeric enrichment reaction for obtaining proton pump inhibitors of formula 1, notably titanium (IV) (cf. WO 96/02535 and US 2003/0171591A1), vanadium and zirconium (IV) or hafnium (IV) (cf. WO 2004/052882), can be eliminated if desired, as the process of the present invention effectively works with other metals, including well tolerated manganese (Mn).

Secondly, when the amount of metal catalyst of any type of usable metal can be substantially reduced according to the invention without affecting enantiomeric excess, removal of any remainder of catalyst-derived metal is better ensured. Generally, the higher the amount of metal catalyst actually used in the reaction, the lower are the chances of later removing remaining catalyst-derived metal overall. Moreover, as the interaction between catalyst-derived metal with the product in the form of formula 1 may be strong, there can be an inevitable carry-over and thus an unavoidable poisoning of the subsequent processing in the salting step. As a consequence and further relevant in terms of the timing for the final result, essential freeness and more preferably complete freeness of the catalyst-derived metal, which is achievable by the preferable low amount of catalyst and optionally further by a proper selection of metal for the catalyst, is particularly significant at the point after the catalyzed reaction and before salting reaction and subsequently the inclusion of the enantiomerically enriched proton pump inhibitor in a desired form, especially with an pharmaceutically acceptable salt (for example as alkali metal salt such as sodium or potassium, alkaline earth metal salts such as calcium, magnesium or strontium, or ammonium salts), into a pharmaceutical formulation is carried out.

As used herein, the terms "essentially free of catalyst-derived metal" shall mean a control of its amount to be "essentially free" as defined above The term "free of" however may include the presence of at least minimally detectable trace amounts of the respective metal impurity, indicative of whether synthesis went through metal catalysis, and which metal was used in the catalyst, but still up to PDE levels with respect to daily dosage forms indicated above for particularly useful metals. Preferably, the yielded product of formula 1 and consequently the follow-up products of the desired pharmaceutically acceptable salt (e.g. sodium, potassium, magnesium and the like) can be entirely free, even below detection limit, as the use of more critical catalyst-derived metals previously used, notably titanium (IV) and especially zirconium (IV) or hafnium (IV), can be completely avoided according to the present invention if desired. The preferred intermediate and pharmaceutical product obtainable by the present invention can be defined by containing at least detectable amounts or trace amounts of Mn derived from the enantioselective oxidation. Maximum Mn limit can be controlled to a PDE dose level of 2.5 mg/day of Mn or below.

The present invention is illustrated but in no way limited by the following examples:

Analytical Methods

Chemical purity and sulfide/sulfoxide/sulfone ratios were determined by HPLC analysis according to the following method: Symmetry C8 (3.5 μm, 100×4.6 mm) column, flow rate: 1.2 ml/min; detection: UV (280 nm); injection volume: 50 μl, T=30° C.; eluent A: phosphoric buffer/MeCN 82/18 (v/v), eluent B: phosphoric buffer/MeCN 35/65 (v/v) (phosphoric buffer: NaH$_2$PO$_4$xH$_2$O (0.725 g) and Na$_2$HPO$_4$ (4.472 g) is dissolved in water (1 l), then 250 ml of the prepared solution is diluted in 1 l of water):

| t  | % A | % B |
|----|-----|-----|
| 0  | 100 | 0   |
| 5  | 100 | 0   |
| 6  | 90  | 50  |
| 15 | 90  | 10  |
| 30 | 20  | 80  |
| 35 | 20  | 80  |
| 36 | 100 | 0   |
| 46 | 100 | 0   |

Enantiomeric purity was determined by HPLC analysis according to the following method: Chiral Pack AD-H (5 μm, 250×4.6 mm) column; eluent: n-hexane/ethanol/methanol 40/55/5 (v/v/v); flow rate: 1.0 ml/min; detection: UV (300 nm); injection volume: 20 μl; T=30° C.

Examples 1-18

Preparation of enantiomerically enriched 5-methoxy-2-[[(4-methoxy-3,5-dimethyl-2-pyridinyl)methyl]sulfinyl]-1H-benzimidazole (1a) using preformed (salen)metal complexes General procedure: 5-Methoxy-2-[[(4-methoxy-3,5-dimethyl-2-pyridyl)methyl]thio]-1H-benzimidazole (4a) and the (salen)manganese complex 2a-e are dissolved in acetonitrile. The reaction temperature is adjusted, then 30% aqueous H$_2$O$_2$ is added dropwise and the mixture is stirred for several hours. Then the reaction mixture is transferred portion-wise into a cold (0° C.) 10% aqueous solution of Na$_2$SO$_3$ and stirred for additional 15 min. The obtained mixture is extracted with dichloromethane. The organic phase is dried over Na$_2$SO$_4$ and concentrated yielding an oily residue which is analyzed by chiral and achiral HPLC analytical method.

Typically, runs were carried out on 0.5-6 mmol scale of the starting material 4a in acetonitrile (1 mmol 4a in 10 mL MeCN). The amounts of added reagents, temperature and reaction time in particular examples are indicated in Tables 1 to 3. Also the results are indicated in Tables 1-3.

TABLE 1

(examples 1-12). Enantioselective oxidation of 4a.[a]

| Ex. No | R,R Salen-Mn complex (2a) [mol%] | 30% H$_2$O$_2$ [mol equiv] | T [° C.] | t [h] | S-omeprazole (1a) Area % | % ee | Sulfone Area % |
|---|---|---|---|---|---|---|---|
| 1 | 2.5 | 15 | -10 | 28 | 42 | 50 | 2.4 |
| 2 | 2.5 | 45 | -10 | 9.5 | 40 | 56 | 2.4 |
| 3 | 5 | 30 | -10 | 6 | 53 | 52 | 5.0 |
| 4 | 5 | 30 | -10 | 6 | 62 | 52 | 6.0 |
| 5 | 7.5 | 30 | -10 | 4.5 | 42 | 60 | 2.1 |
| 6 | 2.5 | 30 | 0 | 2 | 42 | 58 | 1.0 |
| 7 | 2 | 22 | 0 | 2.5 | 44 | 56 | 3.0 |
| 8 | 2 | 24 | r.t. | 3 | 52 | 36 | 5.0 |
| 9 | 2 | 22 | r.t. | 2.5 | 44 | 56 | 3.0 |
| 10 | 2 | 22 | r.t. | 2.5 | 49 | 52 | 3.0 |
| 11 | 2 | 11 | r.t. | 1 | 55 | 62 | 0.3 |
| 12 | 5[b] | 90 | 35 | 3 | 41 | 40 | 3.4 |

[a]Runs 1-11 were carried out on 0.5-6 mmol scale of 4a in MeCN (1 mmol 4a in 10 mL MeCN).
[b]Run 12: 30 mmol of 4a was used.

TABLE 2

(examples 13-15) [a]

| Ex. No. | S,S Salen complex (2b) [mol%] | 30% H$_2$O$_2$ [mol equiv] | T [° C.] | t [h] | R-omeprazole Area % | % ee | Sulfone Area % |
|---|---|---|---|---|---|---|---|
| 13 | 2 | 25 | r.t. | 3 | 51 | 30 | 5.0 |
| 14 | 2[b] | 25 | r.t. | 1 | 25 | 44 | 1.0 |
| 15 | 2 | 6 | r.t. | 2 | 15 | 59 | 0.2 |

[a] Runs 13-15 were carried out on 0.5-1 mmol scale of 4a in MeCN (1 mmol 4a in 10 mL MeCN)
[b]Reaction is carried out in EtCN instead of MeCN.

TABLE 3

(examples 16-18). Enantioselective oxidation of 4a.[a]

| Ex. No. | Salen-Mn complex [mol %] | 30% H₂O₂ [mol equiv] | T [°C.] | t [h] |
|---|---|---|---|---|
| 16 | 2c (R,R), 2 | 25 | r.t. | 2.5 |
| 17 | 2d (S,S), 2 | 6 | r.t. | 5.5 |
| 18 | 2e (S,S), 2 | 6 | r.t. | 4.5 |

| | HPLC analysis of the crude product | | |
|---|---|---|---|
| | Omeprazole | | Sulfone |
| Ex. No. | Area % | % ee | Area % |
| 16 | 46 | 53 (S) | 2.4 |
| 17 | 6.3 | 49 (R) | 0 |
| 18 | 43 | 3 (R) | 8.5 |

[a] Runs were carried out on 0,5 - 1 mmol scale of 4a in MeCN (1 mmol 4a in 10 mL MeCN).

Example 19

5-Methoxy-2-[[(4-methoxy-3,5-dimethyl-2-pyridyl)methyl]thio]-1H-benzimidazole (4a) (19.74 g, 60 mmol) and (R,R)-(−)-N,N'-bis(3,5-di-tert-butylsalicylidene)-1,2-cyclohexanediamino-manganese(III) chloride 2a (0.953 g, 2.5 mol %) are dissolved in acetonitrile (900 ml). The reaction mixture is cooled to −10° C. and 30% aqueous $H_2O_2$ (275 ml, 45 mol equiv.) is added dropwise over 3 hours. The reaction mixture is stirred for additional 8 hours. HPLC analysis shows formation of 40% of sulfoxide with 56% enantiomeric excess (S-enriched). Then 10% aqueous $Na_2SO_3$ (2 l) is slowly added to the reaction mixture and it is extracted with EtOAc (2×2 l). The combined organic phases dried over $Na_2SO_4$. The concentrated oily residue is further dissolved in 0.1 M NaOH (2 l) and extracted with toluene/acetonitrile (9:1, 2×750 ml). To the water phase 1 M aqueous HCl is added until pH 9.4 and it is extracted with EtOAc (1 l). The EtOAc phase is dried over $Na_2SO_4$ and the solvent evaporated yielding oily residue. After addition of isooctane (100 ml) and subsequent evaporation, 8.9 g of the compound Ia is obtained as a crispy foam with 45% ee (S-enriched) and in 90% purity (contains 3% of sulfone) as determined by HPLC analysis.

Example 20

5-Methoxy-2-[[(4-methoxy-3,5-dimethyl-2-pyridyl)methyl]thio]-1H-benzimidazole (4a) (0.987 g, 3 mmol) and (R,R)-(−)-N,N'-bis(3,5-di-tert-butylsalicylidene)-1,2-cyclohexanediamino-manganese(III) chloride (2a) (0.143 g, 7.5 mol %) are dissolved in acetonitrile (45 ml). The reaction mixture is cooled to −10° C. and 30% aqueous $H_2O_2$ (13.8 ml, 45 mol eqiuv) is added dropwise over 6 hours. The reaction mixture is stirred for additional 2 hours. Then the cold reaction mixture is transferred portionwise into a cold (0° C.) 15% aqueous $Na_2SO_3$ and stirred for additional 15 min. The pH of the mixture is adjusted to 9 and the precipitated salts are filtered off. The filtrate is extracted with dichloromethane (2×75 ml) and the combined organic phases are dried over $Na_2SO_4$. The solvent is evaporated yielding 1.15 g of an oily residue containing 62% of sulfoxide is with 55% ee (S-enriched) and 5% of sulfone. The residue is dissolved in a mixture of toluene/acetonitrile (8:2, 100 ml) and extracted with 0.1 M NaOH (3×50 ml). To the water phase 0.1 M aqueous HCl is added to pH 9.4 and it is extracted with dichloromethane (3×50 ml). The combined organic layers are dried over $Na_2SO_4$ and concentrated yielding a crispy foam (0.60 g). The compound is obtained in 92% purity (3.2% of sulfone, 3.5% of starting sulfide 4a) with 50% ee (S-enriched) as determined by HPLC analysis.

Example 21

5-Methoxy-2-[[(4-methoxy-3,5-dimethyl-2-pyridyl)methyl]thio]-1H-benzimidazole (4a) (0.329 g, 1 mmol) and (S,S)—N,N'-bis(3,5-di-tert-butylsalicylidene)-1,2-cyclohexanediamino copper(II) complex (12.1 mg, 2 mol %) are dissolved in acetonitrile (10 ml). The mixture is cooled on an ice-bath and 30% aqueous $H_2O_2$ (0.62 ml, 6 mol eqiuv) is added dropwise. The mixture is stirred for 3 h at 0° C. and 3 h at room temperature. Then 10% aqueous $Na_2SO_3$ is added to the reaction mixture and it is extracted with dichloromethane. The organic phase is dried over $Na_2SO_4$ and concentrated to afford an oil containing 8% of sulfoxide is with 16% ee (R-enriched) as determined by HPLC analysis.

Example 22

Preparation of enantiomerically enriched 5-methoxy-2-[[(4-methoxy-3,5-dimethyl-2-pyridinyl)methyl]sulfinyl]-1H-benzimidazole (1a) using (salen)metal complexes prepared in situ (S,S)—N,N'-Bis(3,5-di-tert-butylsalicylideneamino)-1,2-diphenylethane (10a) (25.8 mg, 0.04 mmol) and manganese (III) acetylacetonate (7.1 mg, 2 mol %) are dissolved in dichloromethane (5 ml). The mixture is stirred for one hour at room temperature and concentrated to give dark brown solid residue. It is dissolved in acetonitrile (10 ml) and 5-methoxy-2-[[(4-methoxy-3,5-dimethyl-2-pyridyl)methyl]thio]-1H-benzimidazole (4a) (0.329 g, 1 mmol) is added. To an ice-bath cooled mixture is added dropwise 30% aqueous $H_2O_2$ (0.62 ml, 6 mol equiv). Then the reaction mixture is allowed to warm up to room temperature and stirred for 4 hours. 10% Aqueous $Na_2SO_3$ is added and it is extracted with dichloromethane. The organic phase is dried over $Na_2SO_4$ and concentrated yielding an oily residue containing 13% of sulfoxide is with 34% ee (R-enriched) as determined by HPLC analysis.

Examples 23-24

Preparation of enantiomerically enriched 5-methoxy-2-[[(4-methoxy-3,5-dimethyl-2-pyridinyl)methyl]sulfinyl]-1H-benzimidazole (1a) using (salen)metal complexes and $AcONH_4$ as an additive

Example 23

5-Methoxy-2-[[(4-methoxy-3,5-dimethyl-2-pyridyl)methyl]thio]-1H-benzimidazole (4a) (0.987 g, 3 mmol), ammonium acetate (92.5 mg, 1.2 mmol) and (R,R)-(−)—N,N'-bis (3,5-di-tert-butylsalicylidene)-1,2-cyclohexanediaminomanganese(III) chloride (2a) (47.6 mg, 2.5 mol %) are dissolved in acetonitrile (45 ml). The reaction mixture is cooled to −20° C. and 30% aqueous $H_2O_2$ (3.1 ml, 10 mol equiv) is added dropwise over 4 hours. The reaction mixture is stirred for additional 5 hours. 10% Aqueous $Na_2SO_3$ is added and the reaction mixture is extracted with ethyl acetate (3×50 ml). The organic phase is dried over $Na_2SO_4$ and concentrated yielding an oily residue containing 55% of sulfoxide (1a) with 57% ee (S-enriched) and 14% of sulfone as determined by HPLC analysis.

Example 24

5-Methoxy-2-[[(4-methoxy-3,5-dimethyl-2-pyridyl)methyl]thio]-1H-benzimidazole (4a) (0.987 g, 3 mmol) and (R,R)-(−)-N,N'-bis(3,5-di-tert-butylsalicylidene)-1,2-cyclohexanediamino-manganese(III) chloride (2a) (47.6 mg, 2.5 mol %) are dissolved in acetonitrile (45 ml). The reaction mixture is cooled to −20° C. Then a solution of ammonium acetate (232 mg, 3 mmol) and 30% aqueous $H_2O_2$ (13.8 ml, 45 mol equiv) is added dropwise over 3 hours. The reaction mixture is stirred for additional 4 hours. Then 10% aqueous $Na_2SO_3$ is added and extracted with ethyl acetate (3×50 ml). The organic phase is dried over $Na_2SO_4$ and concentrated yielding an oily residue containing 52% of sulfoxide 1a with 49% ee (S-enriched) and 3% of sulfone as determined by HPLC analysis.

Examples 25-26

Preparation of enantiomerically enriched 5-methoxy-2-[[(4-methoxy-3,5-dimethyl-2-pyridinyl)methyl]sulfinyl]-1H-benzimidazole (1a) using (salen)metal complexes and nitrogen containing heterocycles or amines as additives

Examples 25

5-Methoxy-2-[[(4-methoxy-3,5-dimethyl-2-pyridyl)methyl]thio]-1H-benzimidazole (4a) (0.987 g, 3 mmol), chinconine (382 mg, 1.2 mmol) and (R,R)-(–)-N,N'-bis(3,5-di-tert-butylsalicylidene)-1,2-cyclohexanediaminomanganese(III) chloride (2a) (47.6 mg, 2.5 mol %) are dissolved in acetonitrile (45 m). The reaction mixture is cooled to –10° C. and 30% aqueous $H_2O_2$ (3.1 ml, 10 mol equiv) is added dropwise over 4 hours and stirred for additional 3 hours. 10% Aqueous $Na_2SO_3$ is added to the reaction mixture and it is extracted with dichloromethane (3×50 ml). The organic phase is dried over $Na_2SO_4$ and concentrated yielding an oily residue containing 44% of sulfoxide is with 48% ee (S-enriched) and 15% of sulfone as determined by HPLC analysis.

Example 26

(S,S)—N,N'-Bis(3,5-di-tert-butylsalicylidene)-1,2-cyclohexanediamino copper(II) complex (12.1 mg, 2 mol %) is dissolved in acetonitrile (10 ml) and 2,3,5-collidine (2.6 μL, 0.02 mmol) is added. The mixture is stirred for 0.5 h at room temperature. After addition of 5-methoxy-2-[[(4-methoxy-3,5-dimethyl-2-pyridyl)methyl]thio]-1H-benzimidazole (4a) (0.329 g, 1 mmol) the mixture is cooled on ice-bath. 30% Aqueous $H_2O_2$ (0.55 ml, 5 mol equiv) is added dropwise. The reaction mixture is allowed to warm up to room temperature and stirred for 5.5 h. 10% Aqueous $Na_2SO_3$ is added and extracted with dichloromethane. The organic phase is dried over $Na_2SO_4$ and concentrated yielding an oily residue containing 8% of sulfoxide is with 42% ee (R-enriched).

Preparation of Metal Complexes of Salan Chiral Ligands (10b)

A) Synthesis of salan ligands (10b):

Example 27

(R,R)-1,2-bis(3,5-di-tert-butyl-2-hydroxybenzylamino)cyclohexane (R,R)-1,2-bis(3,5-di-tert-butylsalicylidenamino)cyclohexane (5.0 g, 9.2 mmol, 1 mol equiv) is suspended in a mixture of dichloromethane/96% ethanol (1:3, 200 ml). Then $NaBH_4$ (1.74 g, 45.7 mmol, 5 mol equiv) is added portionwise and the mixture is stirred until it becomes colorless (24 h). Water (50 ml) is added to the reaction mixture and it is extracted with dichloromethane (3×50 ml). The combined organic layers are dried over $Na_2SO_4$ and the solvent is evaporated to give the title product as a solid residue (4.95 g, 98% yield): $^1$H NMR (300 MHz, $CDCl_3$) δ 7.30 (1H, d), 6.96 (1H, d), 4.13 (1H, d), 3.99 (1H, d), 2.56 (1H, m), 2.26 (1H, m), 1.78 (1H, m), 1.47 (9H, s), 1.37 (11H, s); $^{13}$C NMR (75 MHz, $CDCl_3$) δ 24.1, 29.6, 30.7, 31.7, 34.1, 34.8, 50.8, 59.8, 122.3, 123.0, 123.1, 135.9, 140.6, 154.3; ESI mass spectrum: 551 [M+H]$^+$.

(Lit.: C. R. Chimie, 2004, 7, 809)

Other salan ligands are prepared according to Example 27 from the corresponding imino analogues:

(S,S)-1,2-bis(2-hydroxybenzylamino)cyclohexane $^1$H NMR (300 MHz, $CDCl_3$) δ 7.18 (1H, dt), 6.99 (1H, dd), 6.83 (1H, d), 6.78 (1H, dd), 4.07 (1H, d), 3.95 (1H, d), 2.48 (1H, m), 2.17 (1H, m), 1.72 (1H, m), 1.23 (2H, m).

(S,S)-1,2-bis(5-methyl-2-hydroxybenzylamino)cyclohexane $^1$H NMR (300 MHz, $CDCl_3$) δ 7.05 (1H, d), 6.84 (1H, d), 6.71 (1H, t), 4.04 (1H, d), 3.90 (1H, d), 2.48 (1H, m), 2.20 (3H, s), 2.14 (1H, m), 1.72 (1H, m), 1.27 (2H, m).

(S,S)-1,2-bis(5-methoxy-2-hydroxybenzylamino)cyclohexane $^1$H NMR (300 MHz, $CDCl_3$) δ 6.80 (1H, d), 6.74 (1H, d), 6.65 (1H, t), 4.03 (1H, d), 3.90 (1H, d), 3.87 (3H, s), 2.42 (1H, m), 2.13 (1H, m), 1.69 (1H, m), 1.23 (2H, m); $^{13}$C NMR (75 MHz, $CDCl_3$) δ 23.9, 30.1, 48.7, 55.6, 60.0, 110.4, 118.5, 120.3, 123.8, 146.4, 147.5; ESI mass spectrum: 387 [M+H]$^+$.

(S,S)-1,2-bis(3,5-di-tert-butyl-2-hydroxybenzylamino)-1,2-diphenylethane $^1$H NMR (300 MHz, $CDCl_3$) δ 10.39 (1H, br s), 7.24 (4H, m), 6.96 (2H, m), 6.63 (1H, m), 4.07 (1H, s), 3.79 (1H, d), 3.62 (1H, d), 1.44 (9H, s), 1.23 (9H, s).

B) Preparation of Metal Complexes of Salan Ligands 10b:

Example 28

Manganese complex of (R,R)-1,2-bis(3,5-di-tert-butyl-2-hydroxy-benzylamino)cyclohexane (R,R)-1,2-bis(3,5-di-tert-butyl-2-hydroxybenzylamino)cyclohexane (0.825 g, 1.5 mmol, 1 mol equiv) and Mn(OAc)$_2$.4H$_2$O (1.103 g, 4.5 mmol, 3 mol equiv) are suspended in 96% EtOH (70 ml). The formed dark brown suspension is refluxed for 2 h. Then anhydrous LiCl (0.191 g, 4.5 mmol, 3 mol equiv) is added and the mixture is refluxed for additional 1.5 h. The reaction mixture is concentrated to one half of the volume and toluene (50 ml) is added. The mixture is washed with water (3×50 ml) and brine (50 ml) and the organic phase dried over $Na_2SO_4$. The solvent is evaporated under reduced pressure and the concentrated dark brown solid residue is formed. It is dissolved in dichloromethane (10 ml) and heptane (15 ml) is added. Dichloromethane is evaporated and a thick suspension is formed. After standing over-night, the obtained precipitate is filtered off.

Preparation of enantiomerically enriched 5-methoxy-2-[[(4-methoxy-3,5-dimethyl-2-pyridinyl)methyl]sulfinyl]-1H-benzimidazole using preformed metal complexes of salan ligands 10b

Examples 29-33

General procedure: 5-Methoxy-2-[[(4-methoxy-3,5-dimethyl-2-pyridyl)methyl]thio]-1H-benzimidazole (4a) and a preformed salan (10b)—metal complex are dissolved in acetonitrile. The reaction temperature is adjusted and 30% aqueous $H_2O_2$ is added dropwise. The mixture is stirred for several hours. Then, it is poured portionwise into a cold (0° C.) 10% aqueous $Na_2SO_3$ and stirred for additional 15 min and extracted with dichloromethane. The organic phase is dried over $Na_2SO_4$ and concentrated yielding an oily residue which is analyzed by chiral and achiral HPLC.

Typically, runs were carried out on 1 mmol scale of the starting material 4a in acetonitrile (1 mmol 4a in 10 mL MeCN). The amounts of added reagents, temperature and reaction time in particular examples are indicated in Table 4. Also the results are indicated in Table 4.

TABLE 4

Enantioselective oxidation of 4a.[a]

| | Reaction conditions | | | | |
|---|---|---|---|---|---|
| | Mn complex of salan ligand | | | | |
| Ex. No. | Salan ligand (10b) | Mn-atom [mol %] | 30% $H_2O_2$ [mol equiv.] | T [° C.] | t [h] |
| 29 | (1S,2S)-cyclohexanediamine bis(2-hydroxybenzyl), S,S | 2 | 6 | 0 and r.t | 2.5 3.5 |
| 30 | (1S,2S)-cyclohexanediamine bis(3-methyl-2-hydroxybenzyl), S,S | 2 | 12 | r.t. | 5.5 |
| 31 | (1S,2S)-cyclohexanediamine bis(3,5-di-t-Bu-2-hydroxybenzyl), S,S | 2 | 6 | r.t | 5.5 |
| 32 | | 2 | 12 | r.t | 5.5 |
| 33 | (1S,2S)-1,2-diphenylethylenediamine bis(3,5-di-t-Bu-2-hydroxybenzyl), S,S | 2 | 6 | r.t. | 5 |

TABLE 4-continued

Enantioselective oxidation of 4a.[a]

HPLC analysis of the crude product

| Ex. No. | 1a | | Sulfone |
|---|---|---|---|
| | Area % | ee % | Area % |
| 29 | 38 | 9 (R) | 2 |
| 30 | 31 | 7 (R) | 1 |
| 31 | 17 | 31 (R) | 0 |
| 32 | 24 | 40 (R) | 0 |
| 33 | 14 | 32 (R) | 0 |

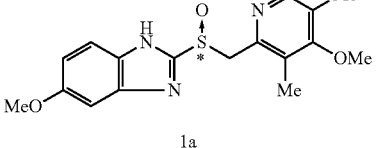

[a]Runs were carried out on 0.5-1 mmol scale of 4a in MeCN (1 mmol 4a in 10 mL MeCN).

Example 34

5-Methoxy-2-[[(4-methoxy-3,5-dimethyl-2-pyridyl)methyl]thio]-1H-benzimidazole (4a) (0.987 g, 3 mmol) and manganese complex of (R,R)-1,2-bis(3,5-di-tert-butyl-2-hydroxybenzyl-amino)cyclohexane (10c) (96 mg, 5 mol %) are dissolved in acetonitrile (45 ml). The reaction mixture is cooled to −10° C. and 30% aqueous $H_2O_2$ (13.8 ml, 45 mol equiv) is added dropwise over 3 hours period. The reaction mixture is stirred for additional 2 hours. HPLC analysis shows formation of 56% of sulfoxide (1a) with 67% ee (S-enriched) and 5% of sulfone.

Example 35

5-Methoxy-2-[[(4-methoxy-3,5-dimethyl-2-pyridyl)methyl]thio]-1H-benzimidazole (4a) (0.987 g, 3 mmol) and manganese complex of (R,R)-1,2-bis(3,5-di-tert-butyl-2-hydroxybenzylamino)-cyclohexane (10c) (144 mg, 7.5 mol equiv) are dissolved in acetonitrile (45 ml). The reaction mixture is cooled to −10° C. and 30% aqueous $H_2O_2$ (13.8 ml, 45 mol equiv) is added dropwise over 3 hours. The reaction mixture is stirred for additional 2 hours. HPLC analysis shows formation of 64% of sulfoxide (1a) with 64% ee (S-enriched) and 6% of sulfone.

Preparation of enantiomerically enriched 5-methoxy-2-[[(4-methoxy-3,5-dimethyl-2-pyridinyl)methyl]sulfinyl]-1H-benzimidazole using metal complexes of salan ligands 10b prepared in situ Example 36

(S,S)-1,2-bis(2-hydroxybenzylamino)cyclohexane (13.2 mg, 0.04 mmol) and manganese(III) acetylacetonate (7.0 mg, 2 mol %) are dissolved in chloroform (6 ml). The mixture is stirred for one hour at room temperature. Dark brown solution is formed. After addition of 5-methoxy-2-[[(4-methoxy-3,5-dimethyl-2-pyridyl)methyl]thio]-1H-1-benzimidazole (4a) (0.329 g, 1 mmol) the mixture is cooled on an ice-bath and 30% aqueous $H_2O_2$ (0.62 ml, 6 mol equiv) is added dropwise. The reaction mixture is stirred for 1.5 h at 0° C. and for additional 4 hours at room temperature. 10% Aqueous $Na_2SO_3$ is added and the mixture is extracted with dichloromethane. The organic phase is dried over $Na_2SO_4$ and concentrated yielding an oily residue containing 10% of sulfoxide (1a) with 46% ee (R-enriched) as determined by HPLC analysis.

Example 37

(S,S)-1,2-Bis(2-hydroxybenzylamino)cyclohexane (13.2 mg, 0.04 mmol) and of iron(III) acetylacetonate (7.0 mg, 2 mol %) are dissolved in chloroform (5 ml). The mixture is stirred for one hour at room temperature. A dark red solution is formed. After addition of 5-methoxy-2-[[(4-methoxy-3,5-dimethyl-2-pyridyl)methyl]thio]-1H-benzimidazole (4a) (0.329 g, 1 mmol) the mixture is cooled on an ice-bath and 30% aqueous $H_2O_2$ (0.12 ml, 1 mol eqiuv) is added dropwise. The reaction mixture is stirred for 1 hour at 0° C. and for additional 4.5 hours at room temperature. 10% Aqueous $Na_2SO_3$ is added and extracted with dichloromethane. The organic phase is dried over $Na_2SO_4$ and concentrated yielding an oily residue containing 17% of sulfoxide (1a) with 18% ee (R-enriched) as determined by HPLC analysis.

Preparation of Esomeprazole Magnesium Salt

Example 38

5-Methoxy-2-[[(4-methoxy-3,5-dimethyl-2-pyridyl)methyl]thio]-1H-benzimidazole (4a) (9.87 g, mmol) and (R,R)-(−)-N,N'-bis(3,5-di-tert-butylsalicylidene)-1,2-cyclohexanediamino-manganese(III) chloride (2a) (0.953 g, 5 mol %) are dissolved in acetonitrile (225 ml). The reaction mixture is cooled to −10° C. and 30% aqueous $H_2O_2$ (92 ml, 30 mol eqiuv) is added dropwise over 6 hours. The reaction mixture is stirred for additional 8 hours. HPLC analysis shows formation of 62% of sulfoxide with 52% ee (S-enriched). 10% Aqueous $Na_2SO_3$ (1 l) is slowly added to the reaction mixture. The mixture is extracted with ethyl acetate (2×1 l). The combined organic phases are dried over $Na_2SO_4$ and concentrated. The resulting oily residue is dissolved in methanol (50 ml) and purified by HPLC chromatography (ChiralPak® AD, 20 μm particle size, eluent methanol).

Combined fractions containing S-omeprazole are concentrated to reach concentration of ca. 400 mg of S-omeprazole/1 ml of MeOH. 6% Solution of $Mg(OMe)_2$ in MeOH (prepared from 0.12 g of magnesium turnings and 9 ml of MeOH with added catalytic amount of dichloromethane) is added to the concentrated solution of S-omeprazole. The reaction mixture is stirred for half an hour at room temperature under inert atmosphere. Then it is slowly poured into methyl t-butyl ether (320 ml) under vigorous stirring. The formed suspension is cooled to −10° C. and kept at this temperature for an hour. After filtration and washing with methyl t-butyl ether (32 ml) the solid is dried at 40° C. under vacuum to get 3.63 g of S-omeprazole magnesium salt with 99.6% ee and 0.14% of sulfone.

What is claimed is:

1. A process for the preparation of a proton pump inhibitor of formula 1 from the corresponding sulfide compound of the formula 4:

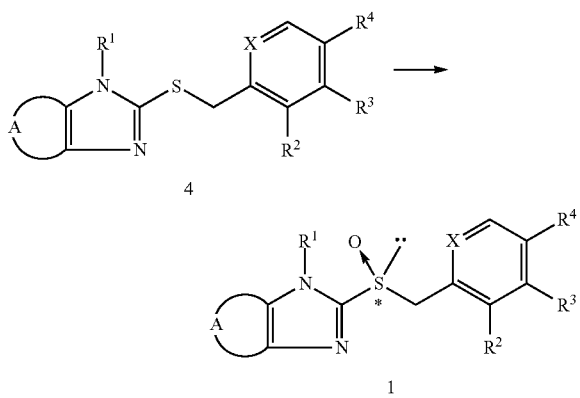

wherein:

S* represents a chiral sulfur atom;

ring A represents benzene or pyridine ring optionally having a substituent independently selected from the group consisting of halide, cyano, nitro, alkyl selected from $C_1$-$C_6$ optionally substituted, aryl, hydroxy, $OR^5$, $C(O)R^5$, and $COOR^5$, wherein $R^5$ is selected from $C_1$-$C_6$ alkyl;

X represents a nitrogen atom;

$R^1$ represents a hydrogen atom;

$R^2$, $R^3$, and $R^4$ can each be a hydrogen atom, or are independently selected from the group consisting of $C_1$-$C_6$ alkyl, $OR^{10}$, and $COOR^{10}$, wherein $R^{10}$ is selected from $C_1$-$C_6$ alkyl;

comprising:

oxidizing the compound of formula 4 in a solvent with an oxygen atom donor in a presence of a metal complex, wherein said metal complex is prepared from an optically active ligand, which is selected from the group consisting of: salen-type complexing ligands, salan-type complexing ligands, and complexing ligands having bidentate, tridentate or tetradentate azomethine or hydrogenated azomethine groups; and a metal precursor comprising a metal selected from the group consisting of Mn, Cu, and Fe.

2. The process according to claim 1, wherein the metal complex is defined by formula 9

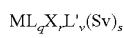

wherein:

M represents a transition metal selected from the group consisting of Mn, Cu, and Fe;

L represents an optically active compound of formula 10

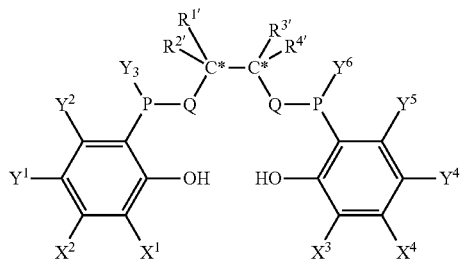

wherein:

C* represents an asymmetric carbon atom;

$R^{1'}$ and $R^{4'}$ are identical and selected from either a first group consisting of a hydrogen atom, $CH_3$, $C_2H_5$, and other primary alkyls or from a second group consisting of aryls, secondary or tertiary alkyls, and alkyls bearing hetero atoms, or $R^{1'}$ and $R^{4'}$ are linked to each other forming a $C_3$-$C_6$ hydrocarbon chain in such a way that $R^{1'}$ and $R^{4'}$ are trans to each other;

$R^{2'}$ and $R^{3'}$ are identical and are either selected from said second group if $R^{1'}$ and $R^{4'}$ are selected from said first group or selected from said first group if $R^{1'}$ and $R^{4'}$ are selected from said second group;

$X^1$ and $X^3$ are independently selected from the group consisting of aryls, primary alkyls, secondary alkyls, tertiary alkyls, and hetero atoms;

$X^2, X^4, Y^1, Y^2, Y^3, Y^4, Y^5$ and $Y^6$ are independently selected from a group consisting of a hydrogen atom, a halide, alkyl, aryl, and alkyl groups optionally bearing hetero atoms;

segment P-Q represents C=N or CH—NH in which one or more hydrogen atoms on coordinating atoms are optionally removed by coordination to the central metal atom X is optionally present and is an anion to balance metal oxidation state and is selected from the group consisting of inorganic ions, and substituted or unsubstituted alkanoates;

L' is optionally present and represents a co-ligand;

Sv is optionally present and represents another ligand than L and L';

q is an integer of 1 or 2, r, v, and s are integers of 0, 1 or 2.

3. The process according to claim 1, wherein the oxidizing is enantioselective and wherein the compound of formula 1 is an S-enantiomer.

4. The process according to claim 2, wherein L is selected from the group consisting of:

salen-type ligands of the formula 10a

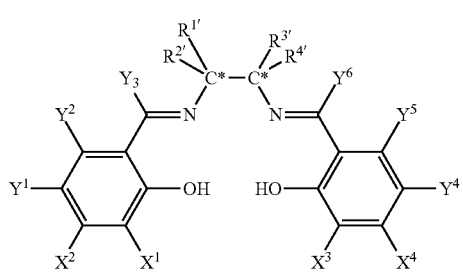

wherein:

C* represents an asymmetric carbon atom;

$R^{1'}$ and $R^{4'}$ are identical and selected from either a first group consisting of hydrogen atom, $CH_3$, $C_2H_5$, and other primary alkyls or from a second group consisting of aryls, secondary or tertiary alkyls, and alkyls bearing hetero atoms, or $R^{1'}$ and $R^{4'}$ are linked to each other forming a $C_3$-$C_6$ hydrocarbon chain in such a way that $R^{1'}$ and $R^{4'}$ are trans to each other;

$R^{2'}$ and $R^{3'}$ are identical and are either selected from said second group if $R^{1'}$ and $R^{4'}$ are selected from said first group or selected from said first group if $R^{1'}$ and $R^{4'}$ are selected from said second group;

$X^1$ and $X^3$ are independently selected from the group consisting of aryls, primary alkyls, secondary alkyls, tertiary alkyls, and hetero atoms;

$X^2, X^4, Y^1, Y^2, Y^3, Y^4, Y^5$ and $Y^6$ are independently selected from a group consisting of hydrogen atom, halide, alkyl, aryl, and alkyl groups optionally bearing hetero atoms; and or L is selected from salan-type ligands of the formula 10b:

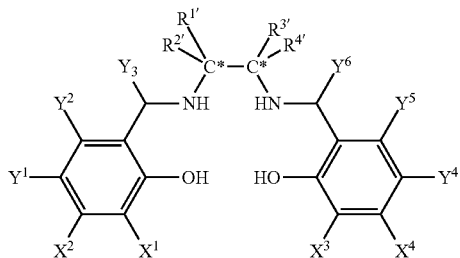

10b wherein:

C* represents an asymmetric carbon atom;

$R^{1'}$ and $R^{4'}$ are identical and selected from either a first group consisting of a hydrogen atom, $CH_3$, $C_2H_5$, and other primary alkyls or from a second group consisting of aryls, secondary or tertiary alkyls, and alkyls bearing hetero atoms, or $R^{1'}$ and $R^{4'}$ are linked to each other forming a $C_3$-$C_6$ hydrocarbon chain in such a way that Rt and $R^{4'}$ are trans to each other;

$R^{2'}$ and $R^{3'}$ are identical and are either selected from said second group if $R^{1'}$ and $R^{4'}$ are selected from said first group or selected from said first group if $R^{1'}$ and $R^{4'}$ are selected from said second group;

$X^1$ and $X^3$ are independently selected from the group consisting of aryls, primary alkyls, secondary alkyls, tertiary alkyls, and hetero atoms;

$X^2, X^4, Y^1, Y^2, Y^3, Y^4, Y^5$ and $Y^6$ are independently selected from a group consisting of hydrogen atom, halide, alkyl, aryl, and alkyl groups optionally bearing hetero atoms.

5. The process according to claim 2, wherein M is Mn and wherein the metal complex has a structure of the formula 2a:

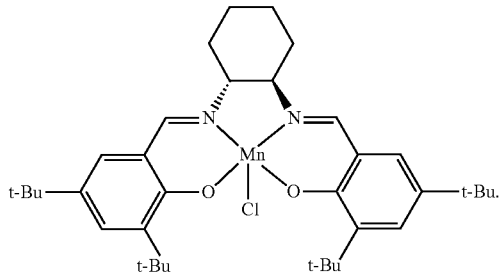

2a

6. The process according to claim 2, wherein L is a compound of formula 10c:

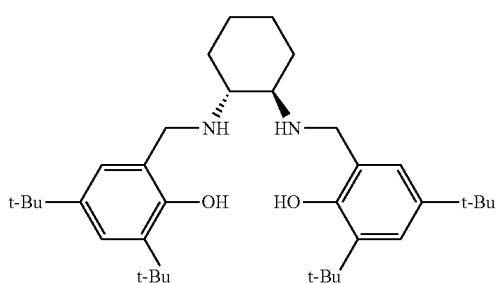

10c wherein the metal complex is prepared by Mn(III) acetylacetonate, Cu(II) acetylacetonate, or Fe(III) acetylacetonate.

7. The process according to claim 1, wherein the process comprises oxidizing the compound of formula 4 in an organic solvent or water or mixture thereof in a temperature range from −40° C. to 40° C. and with a reaction time from 1 hour to 48 hours, and wherein the organic solvent is selected from the group consisting of acetonitrile, acetone, dichloromethane, chloroform, toluene, xylene, methanol and ethanol, and mixtures thereof with water.

8. The process according to claim 1, wherein said metal complex is used in a molar ratio of from 0.005 to 0.1 relative to the compound represented by the formula 4.

9. The process according to claim 1, wherein the oxygen atom donor is selected from the group consisting of hydrogen peroxide, hydrogen peroxide urea complex, organic peroxides, sodium hypochlorite, calcium hypochlorite and peroxy acids.

10. The process of claim 1, further comprising:
optionally forming a salt of the compound of formula 1; and
forming a pharmaceutically acceptable product comprising the compound of formula 1 or a salt thereof.

11. The process of claim 1, wherein the metal complex comprises Mn.

12. The process according to claim 1, wherein the proton pump inhibitor of formula 1 is selected from the group consisting of omeprazole, rabeprazole, pantoprazole, lansoprazole, leminoprazole, tenatoprazole, and their pharmaceutically acceptable salts.

* * * * *